(12) United States Patent
Gao

(10) Patent No.: US 10,029,019 B1
(45) Date of Patent: Jul. 24, 2018

(54) METHOD FOR MITIGATING OSTEOPOROSIS USING METALLIC GOLD CLUSTER MOLECULES

(71) Applicant: Xueyun Gao, Beijing (CN)

(72) Inventor: Xueyun Gao, Beijing (CN)

(*) Notice: Subject to any disclaimer, the term of this patent is extended or adjusted under 35 U.S.C. 154(b) by 25 days.

(21) Appl. No.: 15/455,429

(22) Filed: Mar. 10, 2017

Related U.S. Application Data

(60) Provisional application No. 62/448,700, filed on Jan. 20, 2017.

(51) Int. Cl.
*C01G 7/00* (2006.01)
*A61K 47/64* (2017.01)
*A61K 33/24* (2006.01)
*A61K 9/00* (2006.01)

(52) U.S. Cl.
CPC .......... *A61K 47/643* (2017.08); *A61K 9/0053* (2013.01); *A61K 33/24* (2013.01)

(58) Field of Classification Search
None
See application file for complete search history.

(56) References Cited

U.S. PATENT DOCUMENTS

| | | |
|---|---|---|
| 8,383,919 B2 | 2/2013 | Gao |
| 9,090,660 B2 | 7/2015 | Gao |
| 2017/0304408 A1 | 10/2017 | Gao |

FOREIGN PATENT DOCUMENTS

CA 2767428 A1 1/2011

OTHER PUBLICATIONS

Jie Zheng, et al, "Highly Fluorescent Noble-Metal Quantum Dots," Annu. Rev. Rhys, Chem. 2007. 58:409-31 (filed by applicants in the related U.S. Appl. No. 15/135,890) (Year: 2007).*

Lee, Acsnano, vol. 8, No. 5, 4790-4798, 2014 (The reference available in the related U.S. Appl. No. 15/135,890) (Year: 2014).*

Das, Journal of Stem Cells, vol. 7, 189-199, 2012 (Year: 2012).*

Prosecution History Material for U.S. Appl. No. 15/135,890, including Notice of Allowance, Background Publication about goldclusters, application response to rejection, and Inventor's 37CFR 1.132 declaration and experiment result of peptides.

Ok-Joo Sul, Gold Nanopariticles Inhibited the Receptor Activator of Nuclear Factor-κB Ligand (RANKL)-Induced Osteoclast Formation by Acting as an Antioxidant, Biosci. Biotechnol. and Biochem., 2010, vol. 74, Issue 11, 2209-2213.

Liu Dandan, The effects of gold nanoparticles on the proliferation, differentiation, and mineralization function of MC3T3-E1 cells in vitro, Chinese Science Bulletin, Apr. 2010, vol. 55, Issue 11, 1013-1019.

Masaru Ishii, Sphingosine-1-phosphate mobilizes osteoclast precursors and regulates bone homeostasis, Nature, Mar. 26, 2009, vol. 458, 524-528.

Dong-Zhu Li, Treatment with hydrogen molecules prevents RANKL-induced osteoclast differentiation associated with inhibition of ROS formation and inactivation of MAPK, AKT and NF-kappa B pathways in murine RAW264.7 cells, Journal of Bone Mineral Metabolism, Sep. 2014, vol. 32, Issue 5, 494-504.

Fanord F, Bisphosphonate-modified gold nanoparticles: a useful vehicle to study the treatment of osteonecrosis of the femoral head., Nanotechnology, Jan. 21, 2011; vol. 22, Issue 3, 035102.

Wan-Kyu Ko, The effect of gold nanopaticle size on osteogenic differentiation of adipose-derived stem cells, Journal of Colloid and Interface Science, Jan. 2015, vol. 438, 68-76.

* cited by examiner

*Primary Examiner* — Satyanarayana R Gudibande
(74) *Attorney, Agent, or Firm* — Jie Tan; JT Law Services, PC

(57) ABSTRACT

A therapeutic method for mitigating bone loss. This method includes preparing and administering to animals intraperitoneally or orally a therapeutic agent containing metallic gold cluster molecules as an active ingredient.

16 Claims, 14 Drawing Sheets

METHOD FOR MITIGATING OSTEOPOROSIS USING METALLIC GOLD CLUSTER MOLECULES

CROSS-REFERENCE

Priority is claimed from the U.S. Provisional Patent Application Ser. No. 62/448,700, filed on Jan. 20, 2017, entitled "Method for Mitigating Osteoporosis With Gold Nano-particles," the entirety of which is hereby incorporated by reference for all purposes.

DESCRIPTION OF RELATED ART

The present application relates to osteoporosis treatment and more particularly to a method of using metallic Au(0)-peptide cluster molecules as agents in mitigation of bone loss in animals.

Note that the points discussed below may reflect the hindsight gained from the disclosed inventions, and are not necessarily admitted to be prior art.

Osteoporosis is a detrimental disease that affects 54 million Americans today with about 1 in 2 women and 1 in 4 men who will be affected by the time they reach the age of 50. Osteoporosis is caused by the lack of bone formation or from too much bone decomposition. This syndrome eventually leads to a more fragile bone structure. People suffering from osteoporosis tend to have bone fractures more frequently. The underlying mechanisms of bone formation and decomposition (or resorption) include the cellular actions of osteoblast cells and osteoclast cells. Osteoblasts conduct bone formation through a calcium formation matrix while osteoclasts remove bone by resorption of the crystalline matrix back into extracellular calcium. Many molecular pathways are affected by hormones and other environmental factors that induce osteoclast formation. For example, genetic factors that can lead to reduced estrogen or prostaglandin are possible causes of osteoclast over-abundance. Environmental factors such as alcohol, smoking, low body mass index, poor nutrition, vitamin D deficiency, eating disorders, insufficient exercise, and low dietary calcium intake are all possibilities in afflicting osteoporosis. Oxidative stress can also induce osteoclast formation and with the combination of the above factors can lead to osteoporosis by the time a person reaches the age of 50.

Osteoclasts are multinucleated bone cells that dissemble and digest bone minerals by secreting acid and a collagenase, this process is known as bone resorption. Osteoclasts are located on the endosteal bone surfaces, a thin vascular membrane of connective tissue that lines the inner surface of bone. Osteoclasts differentiate from precursor cells similar to that of macrophages known as Granulocyte-Macrophage Colony Forming Units (CFU-GM) which in turn become the osteoclast precursors when activated by macrophage colony stimulating factor (M-CSF). These precursors are then activated for differentiation into osteoclasts specifically by the RANKL (or receptor activator of nuclear factor kappa-B ligand) pathway. When NF-κβ(or nuclear factor-κβ) is activated within this molecular pathway, osteoclast differentiation occurs and then the cells migrate onto the bone's surface to conduct resorption. Within this signaling cascade, the enzymes Capthepsin K and Tartrate-resistant Acid Phosphatase (TRAP) promote osteoclast formation. The osteoclast precursor cells fuse together during the RANKL pathway to become the multi-nucleated osteoclasts that conduct bone resorption.

Over-expression of a set of genes, such as Runx2, is associated with osteoporosis through the over-abundance of osteoclast differentiation. This can be caused either through genetic mutation or oxidative stress from free radicals. See Arai, F., et al., (1999) "Commitment and Differentiation of Osteoclast Precursor Cells by the Sequential Expression of C-Fms and Receptor Activator of Nuclear Factor κb (Rank) Receptors," $Journal\ of\ Experimental\ Medicine$, 190 (12), 1741-1754. Osteoclast differentiation through RANKL signaling inhibition has been one of the main focuses of research on osteoporosis treatment. Current possible research for osteoporosis treatment includes lanthanum agents, hydrogen molecules, aloin, honeybee propolis, as well as gold nanoparticles.

Much of the current research on osteoporosis treatment focuses on the inhibition of the RANKL signaling pathway during osteoclast differentiation through in vitro cellular studies of Bone Marrow-derived Monocytes (BMMs) and RAW264.7 cells. RAW264.7 cells are commercially available macrophages that are cultured from mice and can be in induced into osteoclasts for in vitro osteoporosis studies.

Lanthanum, a light rare earth element, has been known for its active physicochemical and biological properties. As the compound, Lanthianum Chloride, it has been able to reduce the inflammatory response of activated NF-κβ signaling within the RANKL signal pathway when up to 200 μM was administered into BMMs in vitro. Gene expression that leads towards osteoclastic differentiation was found to be reduced by 50% with this treatment. See Jiang, C., et al., (2015) "Lanthanum Chloride Attenuates Osteoclast Formation and Function Via the Downregulation of Rankl-Induced Nf-κb and Nfatc1 Activities," $Journal\ of\ Cellular\ Physiology$, 231 (1), 142-151.

Hydrogen molecules were found to inhibit RAW264.7 precursor cells from formation into osteoclasts. The hydrogen was able to suppress gene expression as well as the activation of NF-κβ signal pathways that induce osteoclastogenesis. See Li, D., et al., (2013) "Treatment with hydrogen molecules prevents RANKL-induced osteoclast differentiation associated with inhibition of ROS formation and inactivation of MAPK, AKT and NF-kappa B pathways in murine RAW264.7 cells," $Journal\ of\ Bone\ and\ Mineral\ Metabolism$, 32 (5), 494-504.

The compound, Aloin, is an anthrocyclic glycoside that is derived from the Aloe Vera plant. Using RAW264.7 macrophage cells, Aloin was found to prevent osteoclast differentiation by reducing the NF-κβ signaling cascade in the RANKL pathway as well as reducing oxidative stress. See Pengjam, Y., et al., (2016) "NF-κB pathway inhibition by anthrocyclic glycoside aloin is key event in preventing osteoclastogenesis in RAW264.7 cells," $Phytomedicine$, 23(4), 417-428.

An active component of Honeybee Propolis (a glue-like material used by honeybees when producing honeycombs), Caffeic Acid Phenethyl Ester (CAPE) has been observed to inhibit RANKL-induced NF-κβ activation within RAW 264.7 monocytes during osteoclast differentiation. See Ang, E. S. et al., (2009) "Caffeic acid phenethyl ester, an active component of honeybee propolis attenuates osteoclastogenesis and bone resorption via the suppression of RANKL-induced NF-κB and NFAT activity," $Journal\ of\ Cellular\ Physiology$, 221 (3), 642-649.

Gold nanoparticles have been used in drug delivery and diagnostic imaging. Gold nanoparticles have been found to promote osteogenic differentiation of mesenymal stem cells after endocytosis into the cytoplasm. Pure gold nanoparticles that are prepared by electrical explosion of gold wire in distilled water were found to inhibit osteoclast formation in vitro through the RANKL pathway in bone marrow-derived macrophages. See O. SUL, et al., (2010) "Gold Nanoparticles Inhibited the Receptor Activator of Nuclear Factor-κB Ligand (RANKL)-Induced Osteoclast Formation by Acting as an Antioxidant," *Bioscience, Biotechnology, and Biochemistry*, 74 (11), 2209-2213. However, the size of gold particles was found to affect its effectiveness. Synthesizing 30-50 nm gold nanoparticles by reacting HAuCl4 with tri-sodium citrate in boiling water were found to be the most effective in vitro in causing adipose-derived stem cells to differentiate into osteoblasts. See Ko, W., et al., (2015) "The effect of gold nanoparticle size on osteogenic differentiation of adipose-derived stem cells," *J Colloid and Interface Science*, 438, 68-76.

Metal gold particles are known to be non-toxic and can be a safe agent for therapeutic use. However, pure gold nanoparticles are not stable and are prone to aggregate into large colloidal gold particles which are not biologically active. A number of studies have attempted to develop more stable gold nanoparticles so that they also can be used as therapeutic agents for osteoporosis in vivo. A number of attempts to modify gold nanoparticles have been conducted in order to stabilize it. Not all modifications retain its observed effect on osteoclasts. For example, citrate ion modified gold nanoparticles do not inhibit osteoclastogenesis nor affect osteoclast function while alendronate-modified gold nanoparticles have enhanced effect on inducing osteoclast apoptosis and impairing osteoclast function. See Fanord, F., et al., (2010) "Bisphosphonate-modified gold nanoparticles: a useful vehicle to study the treatment of osteonecrosis of the femoral head," *Nanotechnology*, 22 (3), pp 035102. On the other hand, curcumin conjugated gold nanoparticles (CUR-CGNPs) have RANKL-induced osteoclastogenesis in BMMs, and CUR-CGNPs are also functional in animal models in improving bone density and preventing bone loss. See D. N. Heo, et al., (2014) "Inhibition of Osteoclast Differentiation by Gold Nanoparticles Functionalized with Cyclodextrin Curcumin Complexes," *ACS Nano*, 2014, 8 (12), pp 12049-12062.

Synthesis of either alendronate-modified conjugated gold nanoparticles or curcumin conjugated gold nanoparticles involves complicated chemical reactions and steps. Their cytotoxicity in use is also unknown. Additional and effective osteoporosis mitigation agents are needed.

SUMMARY

The present application discloses a method of mitigating bone loss or osteoporosis by administering gold(0)-peptide cluster molecules, a type of crystalized metal gold particles that are stabilized with gold binding peptide molecules.

Stable metallic gold-peptide cluster molecules are obtained through a previously patented method. In one embodiment, sufficient amount of liquid suspension of metallic gold cluster molecules is intraperitoneally administered to animals having bone loss or osteoporosis.

In one embodiment, sufficient amount of liquid suspension of metallic gold-peptide cluster molecules are orally administered to animals having bone loss or osteoporosis.

BRIEF DESCRIPTION OF THE DRAWINGS

The disclosed application will be described with reference to the accompanying drawings, which show important sample embodiments of the invention and which are incorporated in the specification hereof by reference, wherein.

DETAILED DESCRIPTION OF SAMPLE EMBODIMENTS

Figure 1:
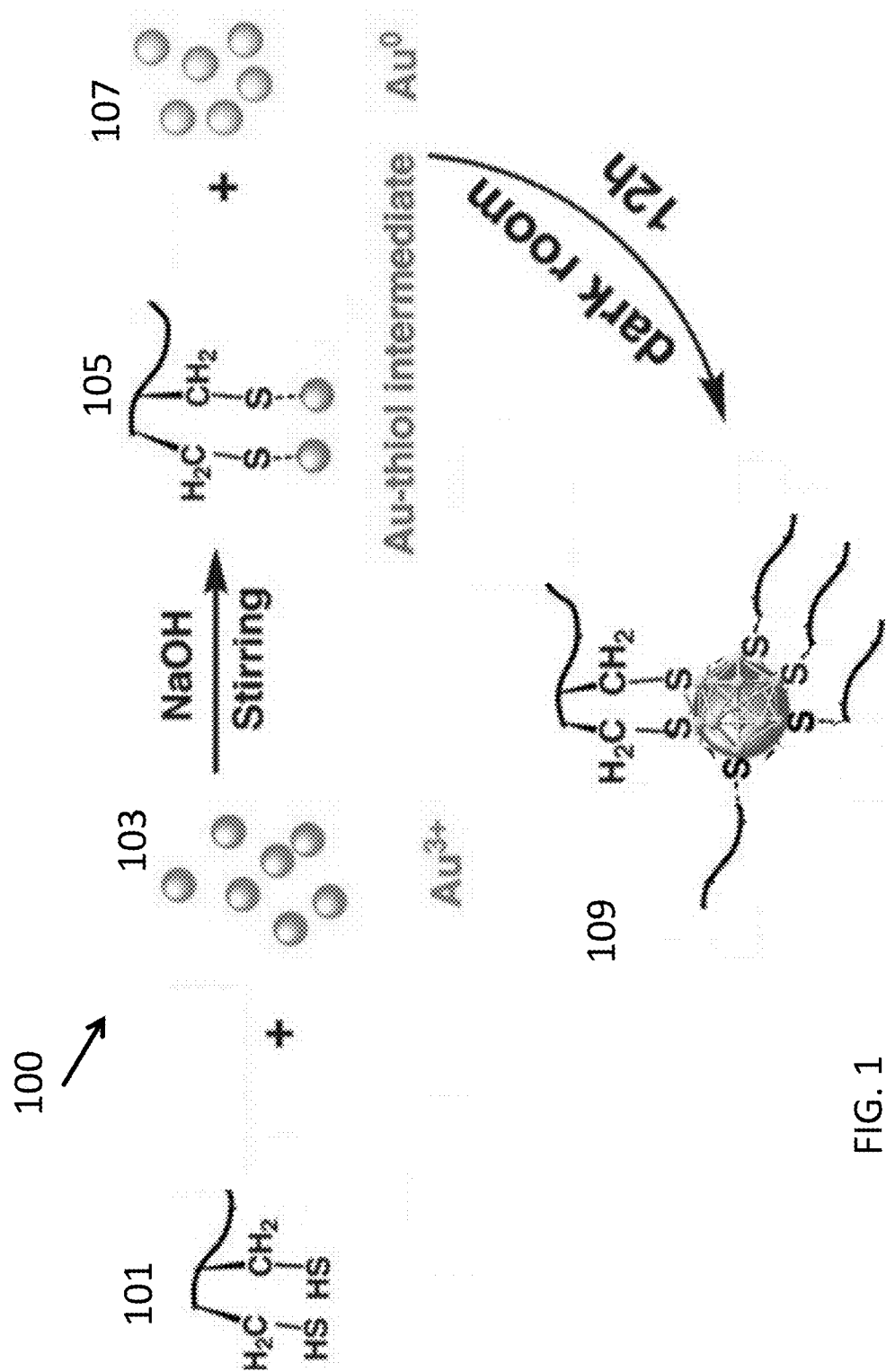
FIG. 1 illustrates an example reaction process for generating metallic gold(0)-peptide cluster molecules.

The numerous innovative teachings of the present application will be described with particular reference to presently preferred embodiments (by way of example, and not of limitation). The present application describes several embodiments, and none of the statements below should be taken as limiting the claims generally.

For simplicity and clarity of illustration, the following figures illustrate the general manner of construction, and description and details of well-known features and techniques that may be omitted to avoid unnecessarily obscuring the invention. Additionally, elements in the figures are not necessarily drawn to scale; some areas or elements may be expanded to help improve understanding of the embodiments of the invention.

The terms "first," "second," "third," "fourth," and the like in the description and the claims, if any, may be used for distinguishing between similar elements and not necessarily for describing a particular sequential or chronological order. It is to be understood that the terms used are interchangeable. Furthermore, the terms "comprise," "include," "have," and any variations thereof, are intended to cover non-exclusive inclusions, such that a process, method, article, apparatus, or composition that comprises a list of elements is not necessarily limited to those elements, but may include other elements not expressly listed or inherent to such process, method, article, apparatus, or composition.

The term "osteoporosis" refers to a bone disease that occurs when the body loses too much bone, makes too little bone, or both. Viewed under a microscope, healthy bone looks like a honeycomb. When osteoporosis occurs, the holes and spaces in the honeycomb are much larger than in a healthy bone. Osteoporotic bones have lost density or mass and contain abnormal tissue structure. As bones become less dense, they weaken and are more likely to break; bones may fracture from a fall, and in serious cases, from sneezing or minor bumps.

The term "metallic gold cluster" refers to the gold-atom cluster molecules wherein the gold atoms form a geometric crystal structure. The gold geometric crystal structure is often stabilized by polymeric capping molecules through forming non-covalent metal bonds with thiol or selenol or phosphine or amine or arginine side group contained in the polymeric molecules. These polymeric molecules can be peptides containing a thiol or arginine or selenol or phosphine or amine side groups. Different to colloidal gold particles, metallic gold cluster molecules usually emit fluorescent emissions under UV excitations. Gold-cluster molecules are generally prepared in mild reductive reaction conditions at room temperature with the presence of polymeric capping molecules in the reaction.

The terms "metallic gold-peptide cluster molecules", "gold(0)$_n$-peptide$_m$", "peptide$_m$-gold$_n$", "Au$_n$-peptide$_m$" and "peptide$_m$-Au$_n$" are used inter-changeably in this application, they all refer to metallic gold cluster molecules that are stabilized by certain peptide molecules via forming metal bonds with a thiol, selenol, phosphine, amine or an arginine side group of peptide or polypeptide molecules, wherein the n and m respectively represents the number of gold atoms and peptide molecules in the cluster. Metallic gold cluster molecules are fluorogenic and structurally different to gold colloidal particles which are not fluorogenic.

The term "gold cluster capping molecule" refers to a thiol or selenol or phosphine or amine or arginine side group containing peptide or polymeric molecule that can form non-covalent metal bonds with gold atoms, thus stabilizing a gold-cluster geometric structure. These molecules include lipids, poly-lysine, poly-arginine, poly-asparagine, poly-aspartic acid sodium salt, poly-aspartic acid sodium salt, poly-glutamate, poly ethylene glycol (PEG), poly(lactic-co-glycolic acid)) (PLGA), protein, polysaccharides, nucleic acid, and their degraded products, bio-polymeric molecules of digestion extracts from various biological sources, including plants, animals, bacteria and fungi, and the standard forms are readily available from a commercial source.

The term "colloidal metallic gold" refers to the high density metal gold particles that are formed by densely packed gold atoms. They are sphere gold particles in a variety of sizes. The colloidal gold particles have no geometric surface other than being round and the number of gold atoms are not predictable. Gold colloidal particles have no fluorescent emission. The most common colloidal gold preparation method is by reacting trisodium citrate, as the reducing agent, in aqueous solution with tetra-chloroaurate dehydrate at an elevated heated temperature close to a boiling or refluxing temperature. See Frens, G., et al., (1973) "Controlled Nucleation for Regulation of Particle Size in Monodisperse Gold Suspensions," *Nature Phys. Sci.* 241, 20-22, the entirety of this article is incorporated by reference.

There are many health problems and a few medical procedures that increase the likelihood of osteoporosis, for example, rheumatoid arthritis (RA), lupus, multiple sclerosis, ankylosing spondylitis, celiac disease, inflammatory bowel disease (IBD), weight loss surgery, leukemia and lymphoma, multiple myeloma, sickle cell disease, stroke, Parkinson's disease, multiple sclerosis (MS), spinal cord injuries, diabetes, hyperparathyroidism, hyperthyroidism, Thalassemia, Cushing's syndrome, thyrotoxicosis, Irregular periods, premature menopause, low levels of testosterone and estrogen in men, depression, eating disorders. Some medicines are also harmful to the bones, such as, aluminum-containing antacids anti-seizure medicine Dilantin® or phenobarbital, Aromatase inhibitors such as ARIMIDEX®, AROMASIN® and FEMARA®, cancer chemotherapeutic drugs, cyclosporine A and FK506 (Tacrolimus), gonadotropin releasing hormone (GnRH) such as LUPRON® and ZOLADEX®, leparin, lithium, medroxyprogesterone acetate for contraception (Depo-Provera®), methotrexate, proton pump inhibitors (PPIs) such as NEXIUM®, PREVACID® and PRILOSEC®, selective serotonin reuptake inhibitors (SSRIs) such as LEXAPRO®, PROZAC® and ZOLOFT®, steroids (glucocorticoids) such as cortisone and prednisone, TAMOXIFEN® (premenopausal use), thiazolidinediones such as ACTOS® and AVANDIA®, thyroid hormones in excess steroid medicines can cause bone loss and osteoporosis.

Normal bone remodeling is a coupled process of bone resorption and formation, and requires coordination of all three types of bone cells, namely osteocytes, osteoblasts and osteoclasts. Irreversible bone loss can result from enhanced bone resorption and/or suppressed bone formation, i.e. an imbalance between osteoclast and osteoblast activities. Under mechanical stress, osteocytes act as mechanosensors to detect changes in the flow of bone fluid within bone canaliculi, and respond by transmitting signals to the osteoblasts via their syncytial processes. Osteoblasts later stimulate osteoclast differentiation and subsequent bone resorption. Normally, osteoblast-mediated bone formation takes place at the same site to fill up the resorption pit with new bone. At the cellular and molecular level, osteoclast-mediated bone resorption commences by osteoblasts initiating proliferation of osteoclast precursors and their differentiation into mature osteoclasts by secreting a cytokine called macrophage colony stimulating factor (MCSF). Osteoblasts also secrete the key mediator for osteoclastogenesis, receptor activator of nuclear factor-κB (RANK) ligand (RANKL), which binds to its receptor (RANK) on the plasma membrane of precursors. This pathway thereby stimulates differentiation of pre-osteoclast osteoclasts into mature osteoclasts. RANKL and MCSF are differentially upregulated by various osteoclastogenic factors, such as parathyroid hormone (PTH), PTH-related peptide and prolactin. Moreover, to counterbalance RANKL action, osteoblasts synthesize and secrete osteoprotegerin (OPG), a soluble decoy receptor capable of inhibiting RANK-RANKL interaction and osteoclastogenesis. In the presence of activated osteoclasts, bone resorption begins with dissolution of inorganic and organic components by hydrochloric acid, cathepsin K and lysosomal protease from osteoclasts. At the molecular level, enhanced bone resorption and osteoporosis generally result, in part, from the overproduction of RANKL and other cytokines/mediators regulating osteoclast differentiation and function. These include cyclooxygenase (Cox)-2, prostaglandin (PG) E2, tumor necrosis factor (TNF)-α, interleukin (IL)-1, IL-6 or IL-11, all of which lead to recruitment and differentiation of pre-osteoclasts. Thus, the greater the increase in the levels of these osteoclastogenic cytokines, the faster the progression of bone loss.

Different to colloidal metallic gold which is densely packed solid gold particle under electronic microscope, peptide-gold cluster molecules are of gold atom clusters with well-defined molecular formula, cluster sizes and stable crystal like structures. Their difference in structure is evidenced by their UV-light absorbent spectra and mass spectrometry. The defined structure and consistency in cluster size provides support for consistency in any of its observed therapeutic effectiveness, rendering gold-cluster molecules a better therapeutic agent. Gold cluster molecules are also different to gold salts whereas gold atoms are in an oxidized status and are usually toxic to the cells, the gold atoms in gold cluster molecules are in zero charge metallic status, therefore maintaining its non-cytotoxic physical property.

Having the advantage of a well-defined molecule complex structure and weight, measurable fluorescent spectra, UV-light absorbent spectra and mass spectrometry, peptide-gold cluster molecules are better suited to be utilized for medical use than colloidal gold.

In this application, peptide-gold-clusters are stabilized by a thiol or selenol or amine or arginine side group of peptides. Cysteine rich peptides act as both as a reductive agent and as a stabilizing agent as shown in a typical chemical reaction for generating peptide-gold cluster complex molecules is illustrated in FIG. 1. Also see U.S. Pat. No. 8,383,919 to Xueyun Gao, the entirety of which is incorporated by reference. In the reaction occurring in FIG. 1, crystal-like metallic gold atom clusters are formed and stabilized by cysteine rich peptides with non-covalent metal bonds. The number of peptide molecules bound to a gold-cluster differs between different peptide sequences. For example, in peptide sequence SEQ ID NO:1 the number of peptide molecules bind to a gold-cluster is 9 while the number of gold atoms is 25, for peptide sequence SEQ ID NO:2 the number of peptide molecules bind to a gold-cluster is 18 and the number of gold atoms is also 25; if using human serum album protein as the reaction agent and capping molecule, the generated gold cluster can contain 4000 gold atoms and an unknown number of album protein molecules. These non-covalent metal bonds formed between peptides and gold crystal atoms allow for competitive bindings of other cysteine rich proteins or peptides in vivo, rendering gold-cluster complex potentially a good non-toxic, non-intrusive therapeutic candidate molecules for regulating cysteine rich proteins in vivo.

Preparation of Metallic Gold-Peptide Cluster Molecules

In preparing stable nano-sized metallic gold clusters using peptides containing tyrosine or cysteine residues, the peptides also function as the stabilizing agent for the crystal-like structure of the metallic gold cluster. Other binding polymeric molecules can also be used as stabilizing agents. These molecules include lipids, poly-lysine, poly-arginine, poly-asparagine, poly-aspartic acid sodium salt, poly-aspartic acid sodium salt, poly-glutamate, PEG, PLGA, proteins, polysaccharides, nucleic acids, and their degraded products, bio-polymeric molecules of digestion extracts from various biological sources, including plants, animals, bacteria and fungi, and the standard forms are readily available from a commercial source.

EXAMPLE 1

For clarity reasons, the example in this application was conducted using a published peptide sequence (SEQ ID NO:1) Cys-Cys-Tyr-Gly-Gly-Pro-Lys-Lys-Lys-Arg-Lys-Pro-Gly. See Liu, R., et al, "The Au Clusters Induce Tumor Cell Apoptosis via Specifically Targeting Thioredoxin Reductase 1 (TrxR1) and Suppressing Its Activity", *Chem. Commun.*, 2014, 50, 10687-10690. The chemical reaction is as the following:

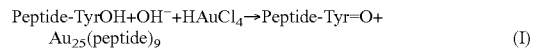

All chemicals were purchased from Sigma-Aldrich, unless otherwise indicated. Ultrapure water was used throughout the experiments. The peptides with 95% purity were chemically synthesized by a solid phase method (China Peptides Co. Ltd.). All glassware were washed with aqua regia, and then rinsed with ultrapure water and ethanol. An aqueous solution of $HAuCl_4$ (25 mM, 80 μ) was slowly added to peptide solution (1.06 mM, 1880 μL) in a 5 mL vial under vigorous stirring at room temperature, then NaOH (0.5 M, 40 μL) was added within 30 seconds to give a final pH of ~10. The sample was sealed and stored in the dark for 15 hours without any disturbance to produce the products. The generated products were dialyzed for 12 hours (Dialysis Tube MWCO=500) to remove free $HAuCl_4$ and NaOH, and the sample was further concentrated by an ultrafiltration tube (Millipore, MWCO: 3000) to remove free peptides. The obtained metallic gold(0)-peptide cluster molecules are suspended in the water and kept in dark at 4° C. for further testing. Structures were tested through UV-spectrum and fluorescent spectrums, and mass spectrometry.

Figure 2B:
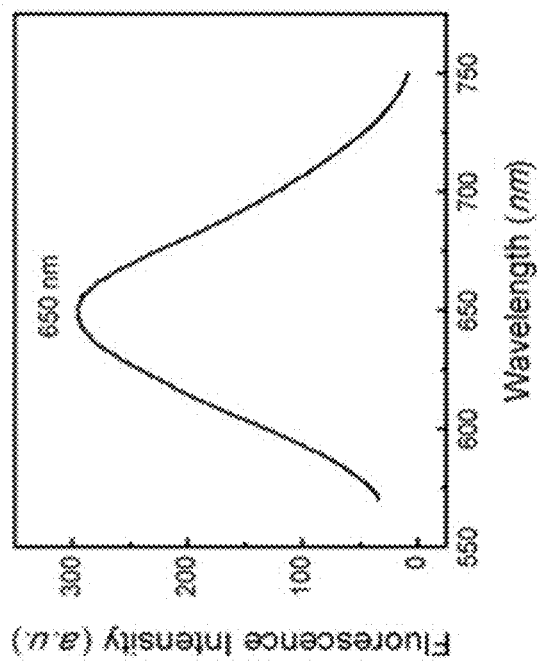
FIG. 2B is the fluorescence spectrum of metallic peptide$_9$-gold$_{25}$ cluster molecules of FIG. 2A thereof in accordance with this application.
Figure 2A:
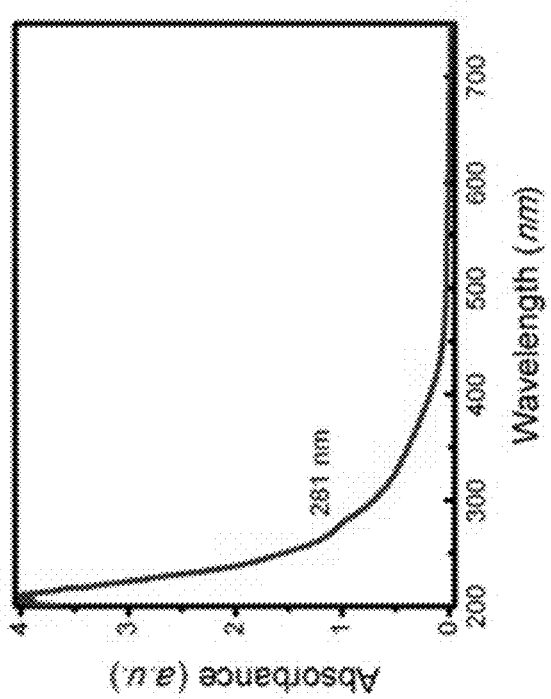
FIG. 2A is the absorbance spectrum of metallic peptide$_9$-gold$_{25}$ cluster molecules having peptides of SEQ ID NO: 1 in accordance with this application.
Figure 2C:
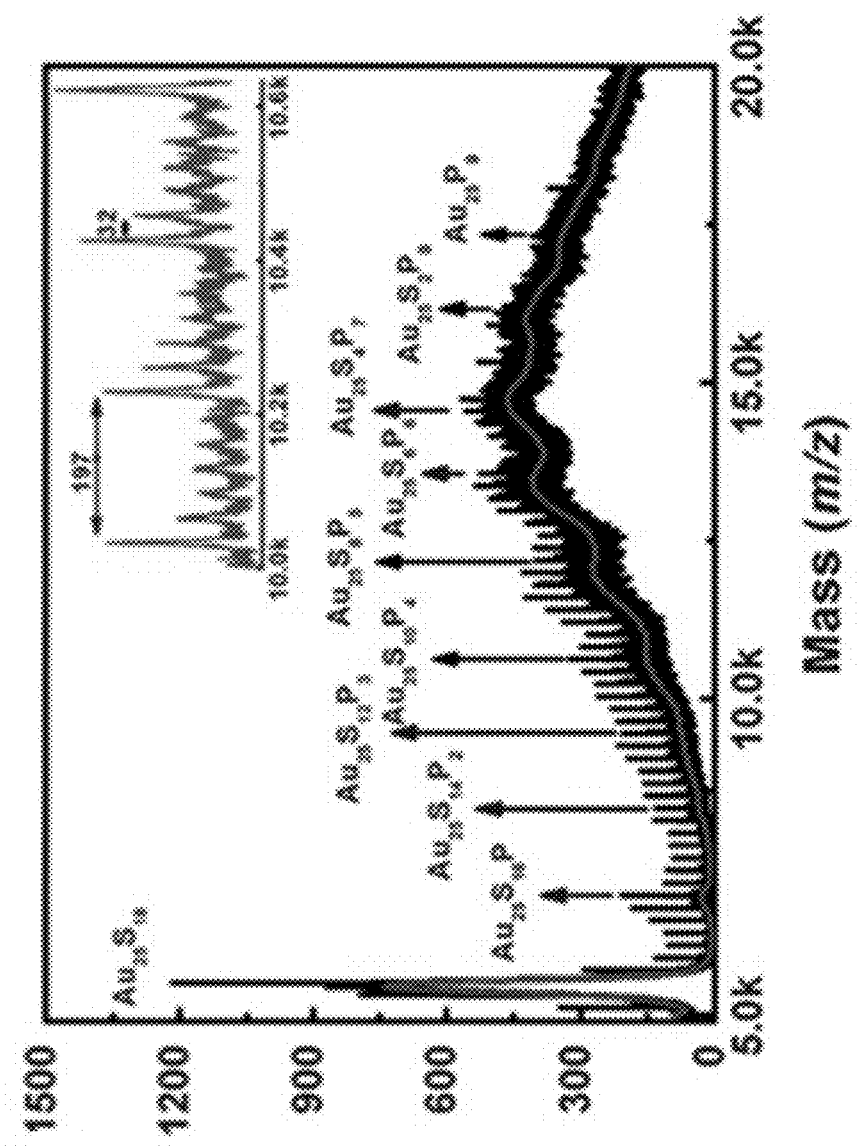
FIG. 2C is the mass spectrometry of metallic peptide$_9$-gold$_{25}$ cluster molecules of FIG. 2A in accordance with this application.

FIGS. 2A and 2B show the absorbance and fluorescence emission peak are located at 281 nm and 650 nm, respectively. The mass spectrometry (FIG. 2C) indicated the generated peptide-gold cluster complex molecules are 25 gold atom clusters having maximum of 9 binding peptide molecules, i.e. $Au_{25}(peptide)_9$.

EXAMPLE 2

Another metallic gold-peptide cluster complex sample was made by using peptide (SEQ ID NO: 2) Glu-Cys-Gly (GSH) with the published procedure similar to the procedure in EXAMPLE 1 with the chemical reaction (II). See Luo, Z., et al, "From Aggregation-Induced Emission of Au(I)-Thiolate Complexes to Ultra bright Au(0)@Au(I)-Thiolate Core-Shell Clusters", *J. Am. Chem. Soc.*, 2012, 134, 16662-16670.

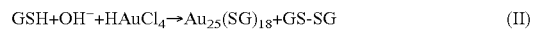

Figure 3A:
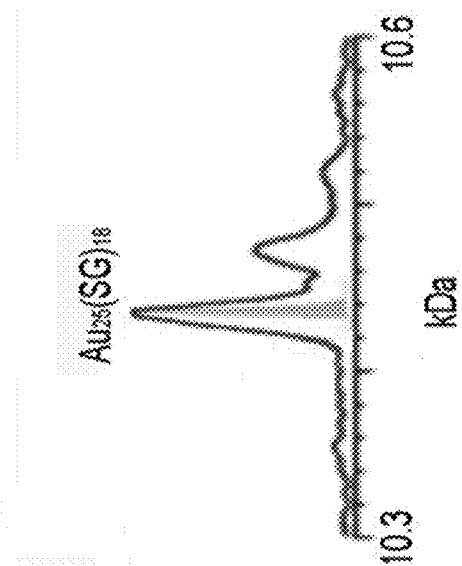
FIG. 3A is the absorbance spectrum of metallic peptide$_{18}$-gold$_{25}$ cluster molecules having peptides of SEQ ID NO: 2 in accordance with this application.
Figure 3B:
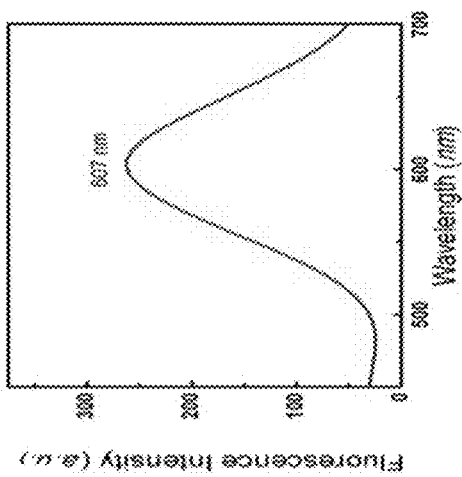
FIG. 3B is the fluorescence spectrum of metallic peptide$_{18}$-gold$_{25}$ cluster molecules of FIG. 3A thereof in accordance with this application.
Figure 3C:
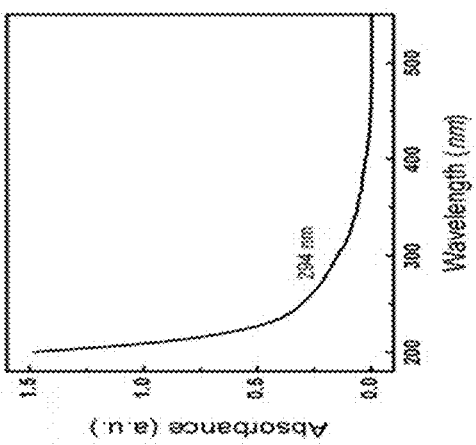
FIG. 3C is the mass spectrometry of metallic peptide$_{18}$-gold$_{25}$ cluster molecules of FIG. 3A thereof in accordance with this application.

FIG. 3C is the mass spectrometry of the generated gold-peptide cluster molecules showing a molecule formula of $Au_{25}(SG)_{18}$. FIGS. 3A and 3B show the absorbance and fluorescence emission spectra of the gold $Au_{25}(SG)_{18}$ cluster molecules. The absorbance and the maximum fluorescence emission peaks are located at 294 nm and 607 nm, respectively.

EXAMPLE 3

Another metallic gold-peptide cluster complex sample is made by using human serum album protein (HSA) with the following chemical reaction:

(III)

Figure 4:
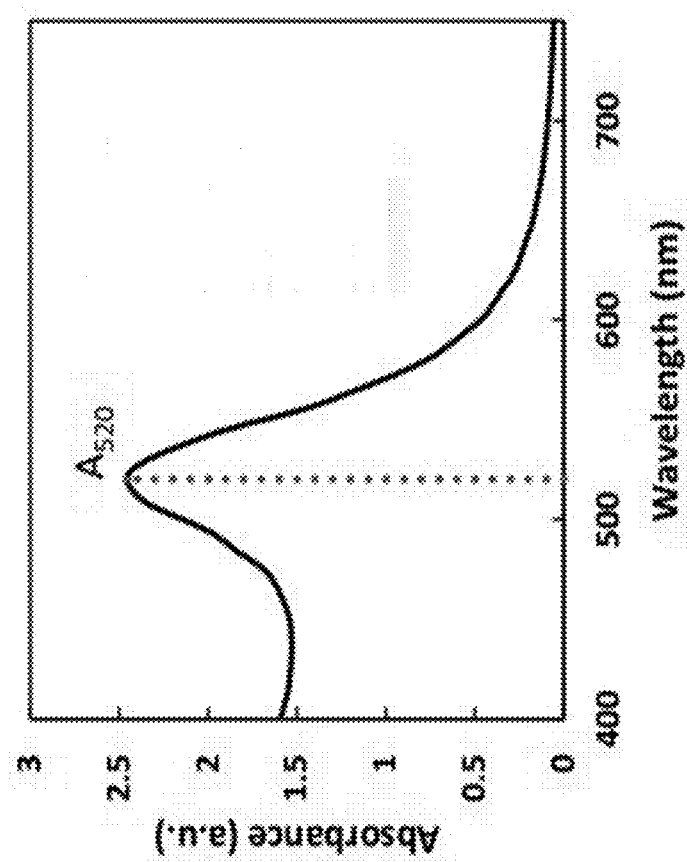
FIG. 4 is the absorbance spectrum of metallic HAS-gold$_{4000}$ cluster molecules in accordance with this application.

All chemicals were purchased from Sigma-Aldrich, unless otherwise indicated. Ultrapure water was used throughout the experiments. All glassware were washed with aqua regia, and then rinsed with ultrapure water and ethanol. Aqueous $HAuCl_4$ solution (5 mL, 10 mM, 37° C.) was added to HAS solution (5 mL, 5 mg/mL, 37° C.) under vigorous stirring. Two minutes later, NaOH solution (0.5 mL, 1 M) was introduced and the reaction was allowed to proceed under vigorous stirring at 37° C. for 12 hours. After the reaction, the sample was concentrated by a dialysis tube (MWCO: 100 kDa) to remove un-reacted free HSA, NaOH and $HAuCl_4$. The obtained HSA-bound AuCs are suspended in the water and kept in dark at 4° C. UV-VIS spectrum (FIG. 4) of HSA-bound metallic gold cluster molecules shows the characteristic absorbance peak at around 520 nm, resulting from characteristic local surface plasma resonance (SPR).

RAW264.7 Cell Culture

Mouse monocyte/macrophage RAW264.7 cells were obtained from the RIKEN Cell Bank located in Tsukuba, Japan. The cells were cultured in DMEM containing 10% heat inactivated FBS, 2 mM glutamine, 100 U/mL penicillin G, and 100 ug/mL streptomycin sulfate and incubated in a humidified chamber. RAW264.7 cells were seeded in 3000 cells/well in 6 well culture plates and cultured for 5 days with 20 ng/mL RANKL solution for osteoclast differentiation. See Pengjam, Y. et al, (2016) "NF-κB pathway inhibition by anthrocyclic glycoside aloin is key event in preventing osteoclastogenesis in RAW264.7 cells," Phytomedicine, 23(4), 417-428.

In Vitro Experiment

Figure 5:
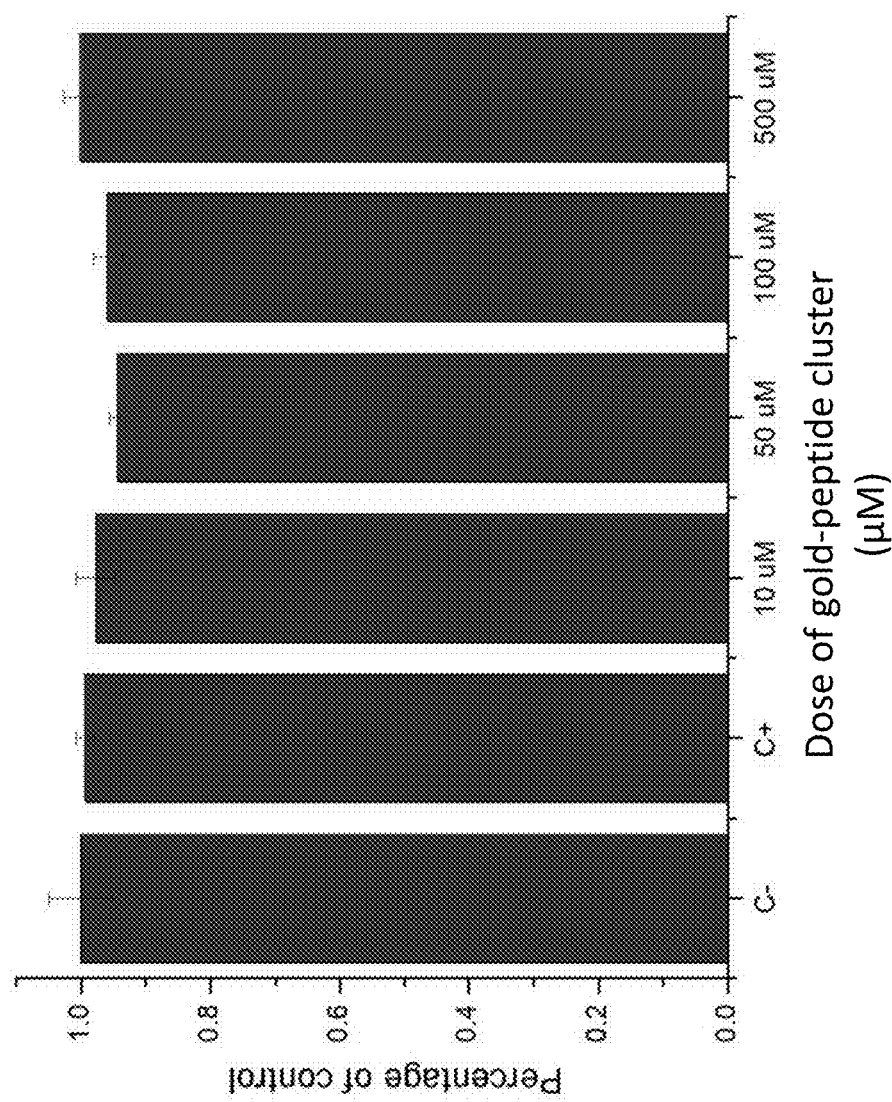
FIG. 5 shows a cytotoxicity test result of peptide-gold cluster molecules upon microphage RAW264.7 cells in accordance with this application.

In reference to FIG. 5, cytotoxicity of peptide-gold cluster molecules was tested using in vitro cultured microphage RAW264.7 cells. Various concentrations of the gold-peptide cluster preparation of Example 1 (10-500 μM) were added to mouse macrophage RAW264.7 cell cultures along with RANKL, cell viability after incubating for 48 hours was measured with a Cell Counting Kit-8 Assay. FIG. 5 shows that there is no measurable cytotoxicity to RAW264.7 cells with gold-peptide cluster molecules up to 500 μM in concentration. The viability of cells without treatment (C⁻) and that of cells with RANKL treatment alone and those of cells treated with both RANKL and gold-peptide cluster molecules are in the same comparable range. Cells treated with as high as 500 μM of gold-peptide cluster molecules are as viable as the non-treated (C⁻) cells.

Tartrate-resistant acid phosphatase (TRAP) is highly expressed by osteoclasts from monocyctes/macrophages and expression can increase during certain pathological conditions like osteoporosis. After RAW264.7 cells were treated with RANKL concentrations, TRAP was assayed for osteoclastogenesis confirmation. TRAP assay kits were obtained from TaKaRa, Bio, Inc. located in Tokyo, Japan, the TRAP assays were conducted based on the manufacturer's instructions.

Figure 6:
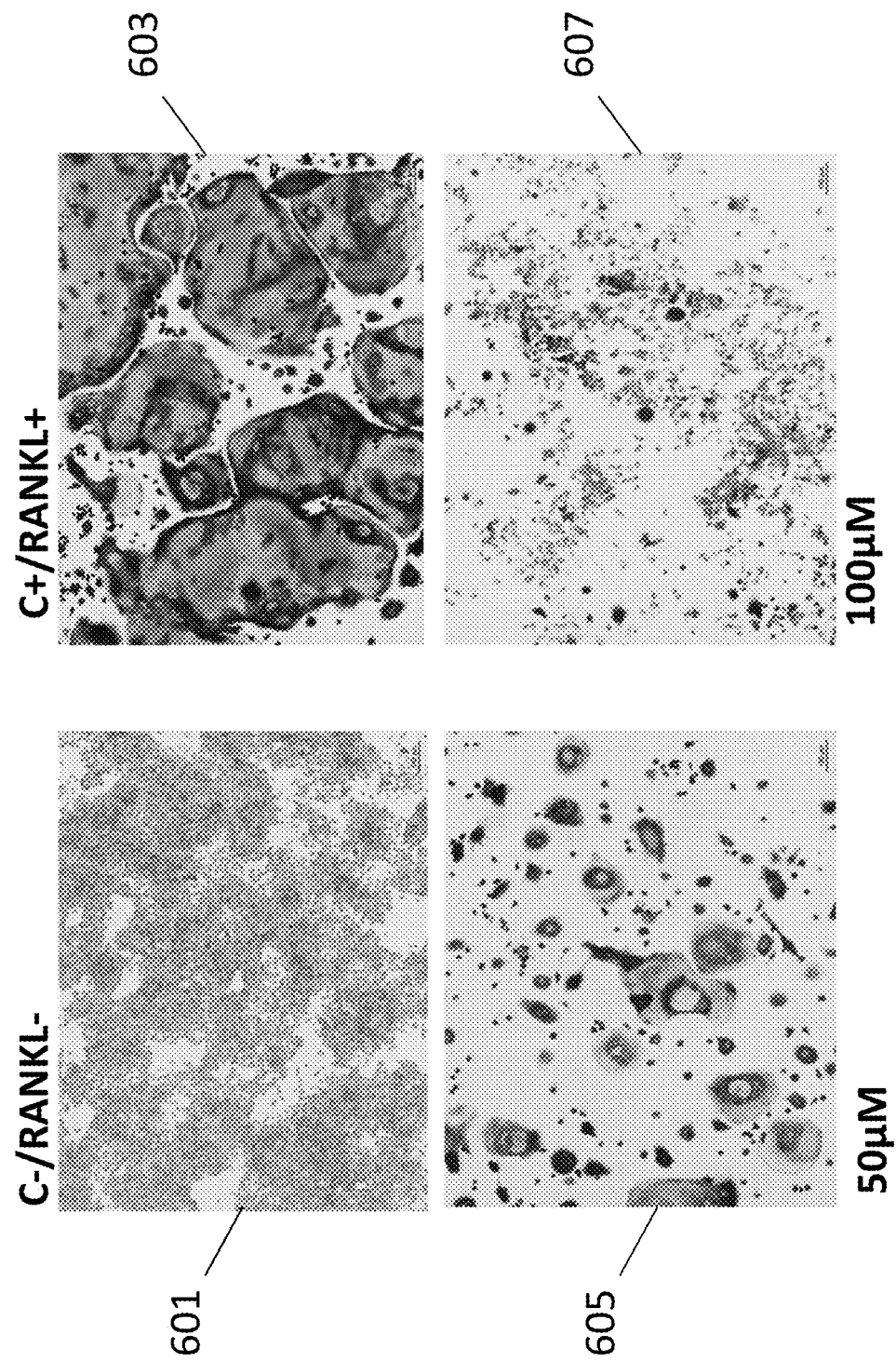
FIG. 6 shows the result of tartrate resistant acid phosphatase (TRAP) staining of RANKL-induced RAW264.7 differentiation into osteoclast cells with or without the presence of peptide-gold cluster molecules in accordance with this application.

In reference to FIG. 6, the inhibitory effect of gold-peptide cluster molecules on the differentiation of macrophage RAW264.7 cell into osteoclasts was measured by TRAP assay. Macrophage RAW264.7 cells were added with various concentrations of gold-peptide cluster molecules along with RANKL, laid for 4 days and stained with the TRAP assay kit. The expression of TRAP-positive stained cells was identified as differentiated cells whereas unstained cells were normal cells. Image 601 shows RAW264.7 cells without influence by RANKL or gold-peptide cluster molecules. The addition of RANKL only shows the depiction of TRAP-positive cells that were stained (Image 603). The addition of gold-peptide cluster molecules at both 50 μM and 100 μM shows the inhibition of TRAP-positive cells when induced with RANKL, with the 100 μM inhibiting the most osteoclast differentiation (Images 605 and 607). Gold-peptide cluster molecules at 50 and 100 μM are capable of inhibiting differentiation of macrophages into osteoclasts.

The inhibitory effect of RANKL induced osteoclast differentiation is further proved with F-actin formation staining. Once RAW264.7 cells differentiate into osteoclast cells, an F-actin ring will form outside the cell membrane. F-actin is an important confirmation of full osteoclast differentiation. For F-actin formation, RAW264.7 cells were seeded into confocal dishes and induced in the presence of RANKL until F-actin rings formed. The process itself takes about five days to complete. After five days of cell culturing, the cells were fixed with 4% paraformaldehyde followed by permeabilization with 0.1% Triton X-100. F-actin rings were stained with actin-stain 555 flourescent phalloidin obtained from Cytoskeleton, Inc. located in Denver, Colo. Rings were then observed using a confocal microscope and Zeiss ZEN software was used to analyze the images. See Jiang, C., et al., (2015) "Lanthanum Chloride Attenuates Osteoclast Formation and Function via the Downregulation of Rankl-Induced Nf-κb and Nfatc1 Activities," *Journal of Cellular Physiology*, 231(1), 142-151.

Figure 7:
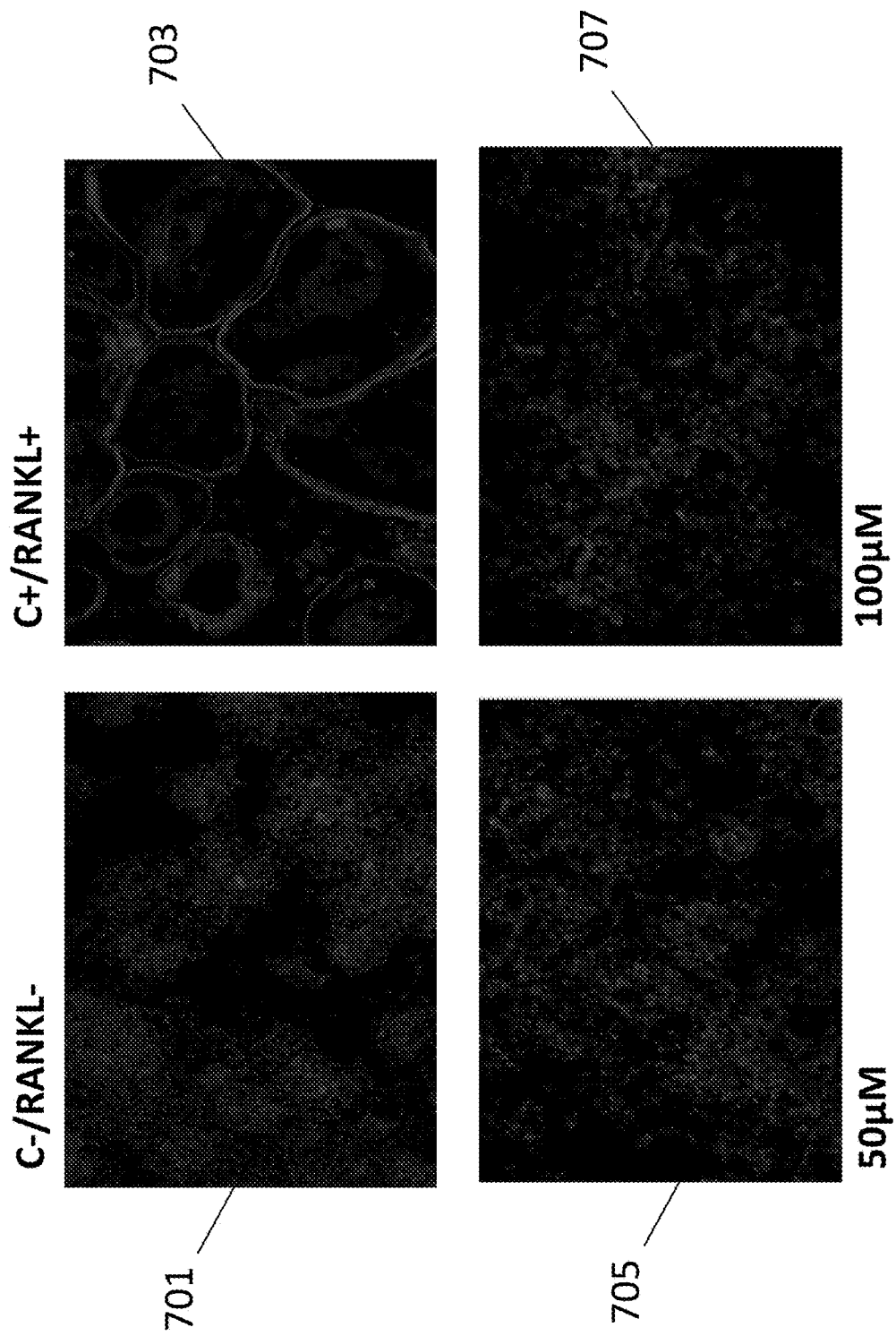
FIG. 7 shows the result of F-actin staining of RANKL-induced RAW264.7 differentiation into osteoclast cells with or without the presence of peptide-gold cluster molecules in accordance with this application.

In reference to FIG. 7, F-actin staining was measured for RANKL-induced differentiated RAW264.7 cells. The experiment added concentrations of 50 and 100 μM of the gold-peptide cluster molecules into RAW264.7 cells along with RANKL for 4 days and then stained with fluorescent phalloidin (F-actin) to analyze for osteoclast differentiation and inhibition. F-actin rings are large actin rings formed when osteoclasts fuse into multi-nucleated cells following differentiation. As shown in FIG. 7, F-actin stains were not prominent with the administration of gold-peptide cluster molecules at both concentrations (Images 705 and 707) and as well as with the lack of induction by RANKL (Image 701). F-actin rings are visible with the induction by RANKL only (Image 703). Gold-peptide cluster molecules are visibly reduced multi-nucleated osteoclast formation by the lack of F-actin positive staining.

Figure 8:
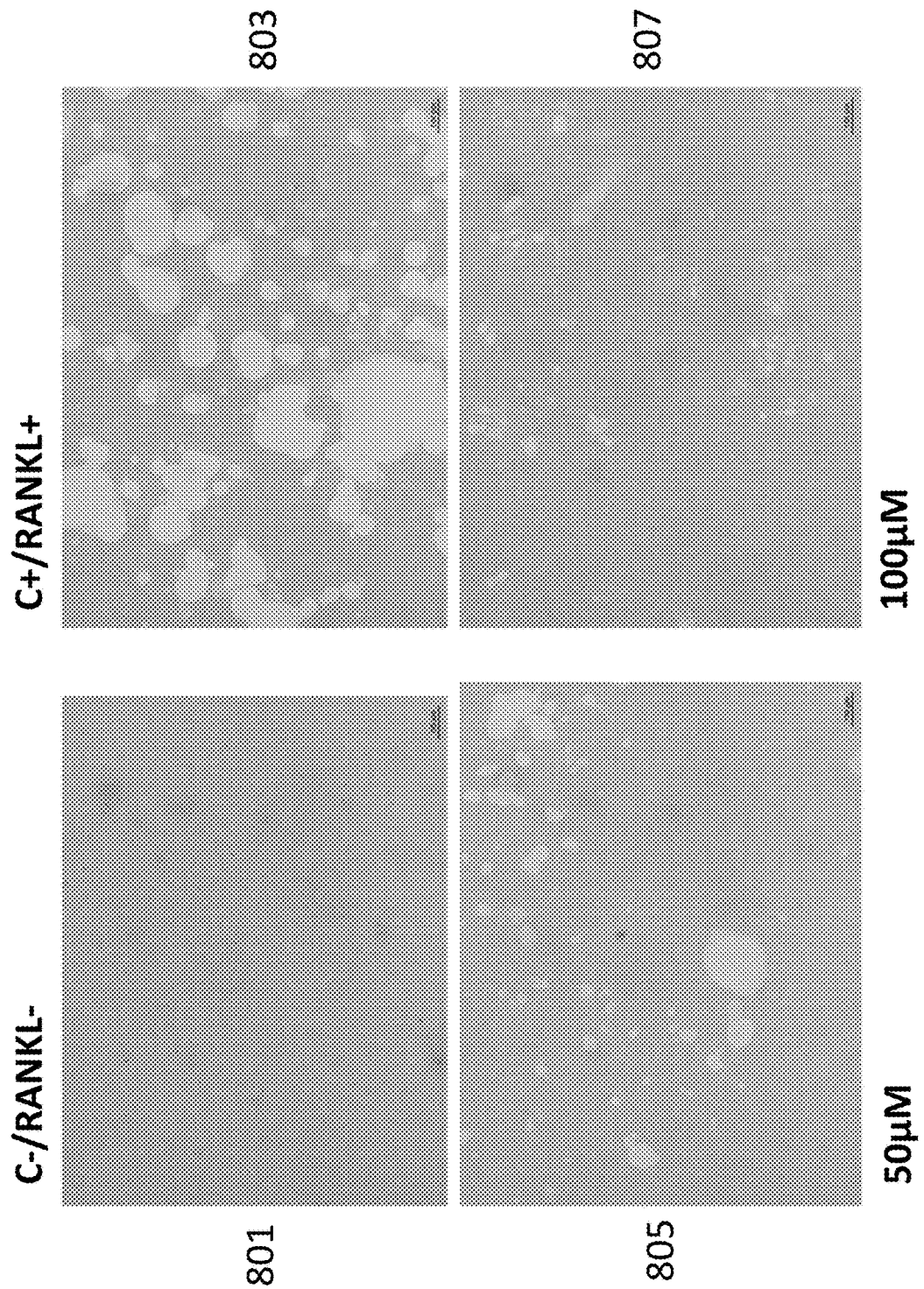
FIG. 8 shows the resulting bone lamella having RANKL-induced RAW264.7 osteoclast cells growing on with or without the presence of peptide-gold cluster molecules in accordance with this application.

In reference to FIG. 8, lacuna assays were further conducted to confirm the relationship between the inhibition of osteoclast differentiation and the inhibition of bone resorption. Slices of mouse model bone were placed in 96-welled plates and incubated with RAW264.7 cells with or without RANKL along with or without gold-peptide cluster molecules for up to 4 days. Bone slices were photographed and analyzed under the microscope. The number of lacunas formed on the bone slices was counted and the percentage of resorption pit area was measured for osteoclast activity. See Jiang, C., et al., (2015), "Lanthanum Chloride Attenuates Osteoclast Formation and Function Via the Downregulation of Rankl-Induced Nf-κb and Nfatc1 Activities," *Journal of Cellular Physiology*, 231(1), 142-151.

FIG. 8 depicts the formation and inhibition of lacunas on bone lamella as a result of RANKL induced or inhibited differentiation of RAW264.7 cells. RAW264.7 cells were cultured and induced to differentiate by RANKL on bone lamella. 50 and 100 µM concentrations of gold-peptide cluster molecules as well as RANKL were added and incubated for 4 days prior to analysis. The RAW264.7 cells were then treated with hypochlorous acid, washed, and stained with 1% toluidine blue to observe formed lacunas on bone lamella under the microscope. Gold-peptide cluster molecules at 100 µM were shown to successfully inhibit bone resorption on bone lamella (Image 807). Bone resorption can be seen following RANKL induction without the treatment of gold-peptide cluster molecules (Image 803). No bone resorption can be observed with the lack of RANKL induction as well as gold-peptide cluster molecules (Image 801). With the addition of 50 µM gold-peptide cluster molecules, RANKL induced number of bone cavities was significantly reduced but as much as 100 µM gold-peptide cluster molecules (Image 805).

The effect of gold-peptide cluster molecules on bone resorption was further verified by western blotting detecting protein kinase phosphorylation. To detect activation of NF-κB signaling pathway, RAW264.7 cells were pretreated with or without gold-peptide cluster molecules for 4 hours followed by stimulation with 50 ng/mL RANKL. The gold-peptide cluster molecules treated or untreated cells were lysed to extract proteins in RIPA/PMSF lysis buffer. Aliquots of the extracts were electrophoresed in sodium dodecyl sulfate (SDS)-polyacrylamide gels in which were transferred into nitrocellulose membranes. The extracts were then blocked with 5% skim milk powder within Tris-buffered saline with Tween 20 (TBST) for 1 hour at room temperature. Target protein bands were visualized by chemiluminescent method and analyzed using Image Lab software. See Jiang, C., et al., (2015). "Lanthanum Chloride Attenuates Osteoclast Formation and Function Via the Downregulation of Rankl-Induced Nf-κb and Nfatc1 Activities," *Journal of Cellular Physiology*, 231(1), 142-151.

Figure 9:
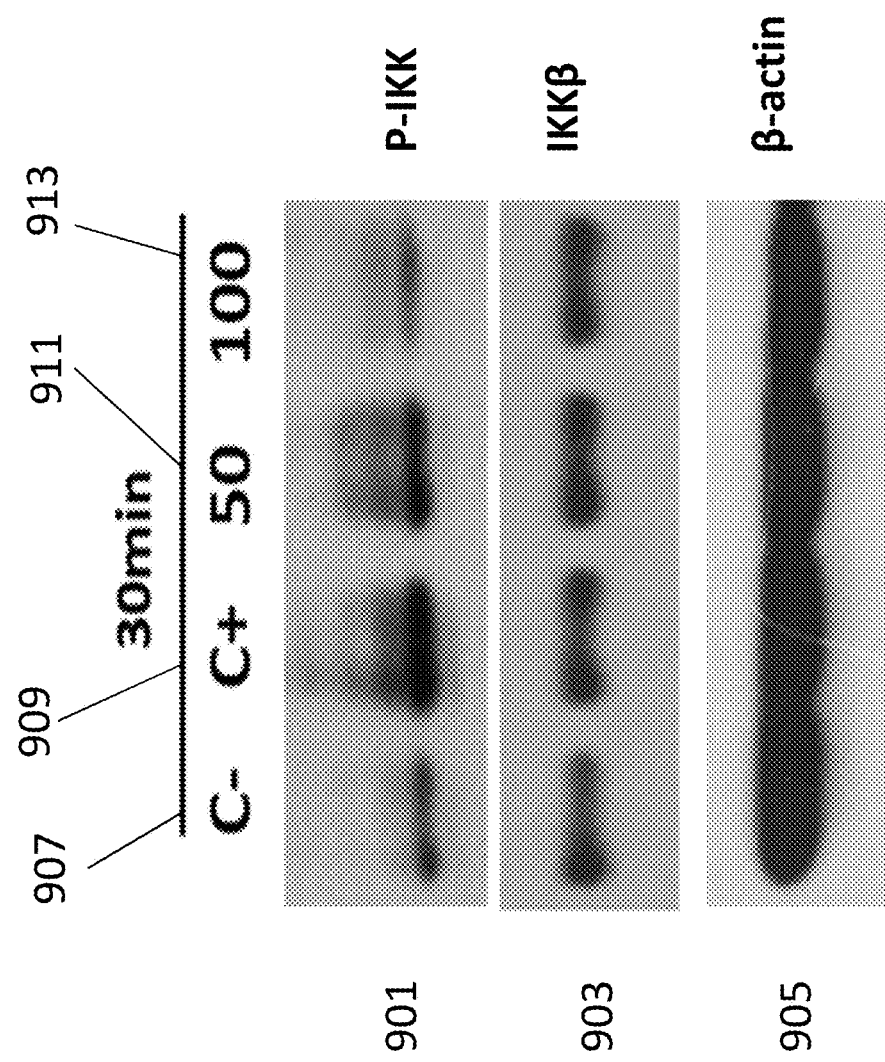
FIG. 9 shows the gene expression result of RANKL-induced RAW264.7 cell osteoclast differentiation with or without the presence of peptide-gold cluster molecules in accordance with this application.

FIG. 9 shows that gold-peptide cluster molecules can effectively inhibit the activation of IKK/NK-kB pathway via inhibiting the RANKL-stimulated phosphorylation IκB protein in RAW264.7 cells. IKK is a kinase which mediates IkB phosphorylation. IKK phosphorylation causes IkB phosphorylation. Phosphorylated IkB (which means P-IKK) degrades through ubiquitin-proteasome system, thereby releasing combined NF-kB. The released NF-kB is transferred to cell nucleus, initiating the transcription of target genes which mark osteoclasts. As RANKL been stimulated, IKK/IkB/NF-kB pathway in RAW264.7 cells is activated. Transcription of osteoclasts-marked target genes is thereby activated. eventually the release of NK-kB that stimulates the gene transcription for RANKL involved cellular differentiation of osteoclasts. Shown in FIG. 9, lane 907 are the control cells without the induction of RANKL, lane 909 are the cells with the induction of RANKL. Lanes 911 and 913 are the cells with the induction of RANKL at the presence of 50 and 100 µM of gold-peptide cluster molecules, respectively. Phosphorylation of signal pathways involved in RANKL cell differentiation are shown with P-IKK (Image 901) compared to the protein level of IKKβ (Image 903) and the expression of β-actin (Image 905). P-IKK phosphorylation (image 901) was reduced with the lack of RANKL activated gene transcriptions (lane 907) but was increased with the addition of RANKL (lane 909). This increase was considerably reduced (lane 911) with 50 µM of gold-peptide cluster molecules, to full inhibition at 100 µM of gold-peptide cluster molecules (lane 913). The expression of IKKβ and β-actin was not affected with the various treatments. FIG. 9 indicates that 100 µM of the gold-peptide cluster molecules can fully inhibit RANKL induced osteoclast differentiation through fully inhibiting the phosphorylation of IKK and its regulated gene transcription.

In vivo Experiment

Collagen induced arthritis and bone loss in animals are used to measure the effects of the gold-peptide cluster molecules on mitigation of osteoporosis in vivo. DBA/1 male mice weighing 20-22 grams were purchased from Hua-Fu-Kang Biotechnology Limited, Beijing, China. Type II collagen and Complete Freund's Adjuvant were purchased from Chondrex Inc., Redmond, Wash., USA. Auranofin was purchased from Sigma, USA and Dexamethasone was purchased from Jin-Yao Amino Acid Company, Tianjing, China. $Gold_{25}(peptide)_9$ gold cluster molecules were prepared according to Example 1.

Type II collagen was dissolved in 0.1 mM acetic acid solution and was emulsified with equal volume of Complete Freund's Adjuvant to make a 1.0 mg/ml Type II collagen emulsion. After one week of resting and environmental adjustment, DBA/1 male mice were divided into groups, each group consisted of 10 mice. Each animal was injected intradermally, at the 2-3 cm base of the tail, an emulsion of 100 µg Type II collagen. On day 21, a second booster dose of 100 µg is Type II collagen emulsion was injected. Negative control groups of mice were injected with an equal amount of 0.9% Sodium Chloride solution.

On day 22, five groups of mice were given different drugs once a day for 28 days (4 weeks) until day 49 (end of week 7). The groups of mice were examined for inflammation and status. Group 1 (normal group) and negative control group (nondrug-treated control group) mice received intragastrically 0.9% Sodium Chloride solution; Group 2 mice received oral administration of 0.5 mg/kg body weight Dexamethasone (Dex); Group 3 mice received oral administration of 1 mg/kg body weight Auranofin; Group 4 mice received oral administration (i.g.) of 50 mg/kg body weight $gold_{25}(peptide)_9$ cluster solution; Group 5 mice received intraperitoneally (i.p.) 5 mg/kg body weight $gold_{25}(peptide)_9$ cluster molecules solution.

The following figures show the typical experimental results mostly from Group 5 of intraperitoneally administering of the gold-peptide clusters while the results from Group 4 of oral administration also showed significant therapeutic effect and improvement in bone structure.

Comparing to the non-treated mice group, intradermal injection of type II collagen immunization induced weight loss in all groups after 1 week of the second booster collagen injection (week 4). Anti-inflammation drug dexamethasone did not reverse the body weight loss, while the entire gold-peptide cluster molecule treated mice groups had slight body weight recovery as seen in FIG. 10.

Figure 10:
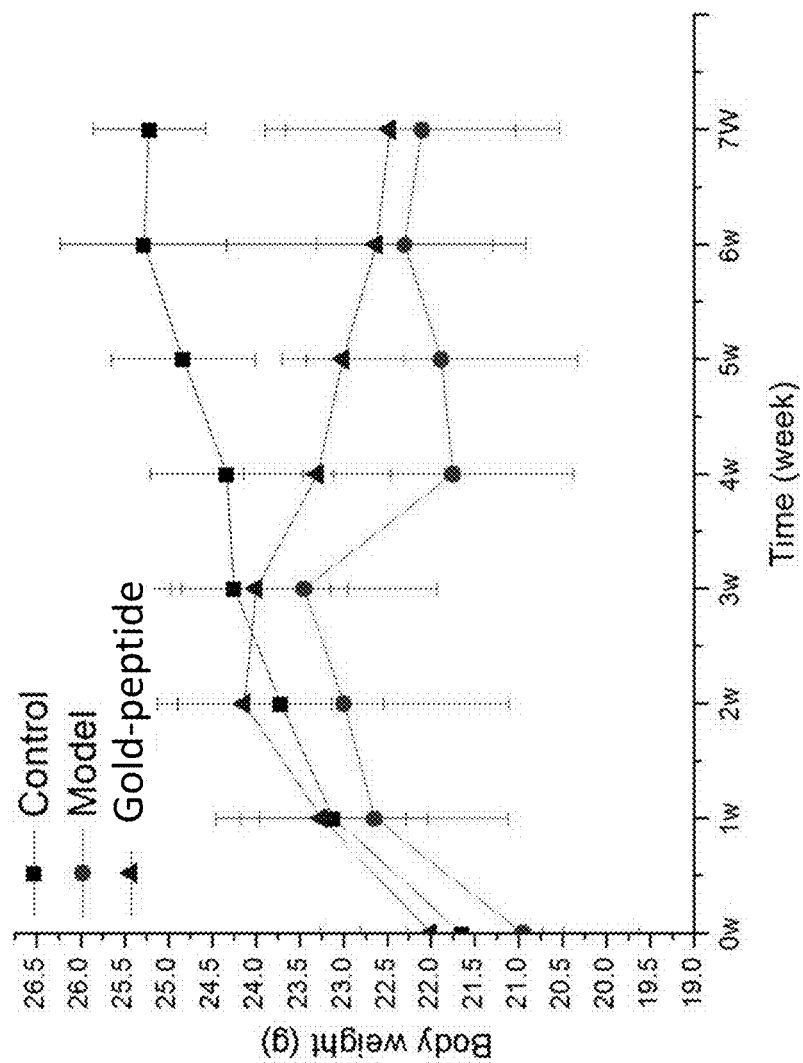
FIG. 10 shows the effect of animal body weight with or without treatment of peptide-gold cluster molecules in accordance with this application.

FIG. 10 displays the weight of the mice when administered with gold-peptide cluster molecules. By injecting gold-peptide cluster molecules in a collagen II-induced mouse model of rheumatoid arthritis, the result showed that it improved the model's weight loss. The control group represents the normal mouse model, the model group represents the mouse model with rheumatoid arthritis, and the drug group represents the mouse model with rheumatoid arthritis with injections of 5 mg/kg $gold_{25}(peptide)_9$ cluster molecule i.p. consecutively for 7 weeks. The figure shows that gold-peptide cluster molecules have no obvious toxicity towards the mouse model and improved overall weight loss of the mouse modeled with rheumatoid arthritis.

Figure 11:
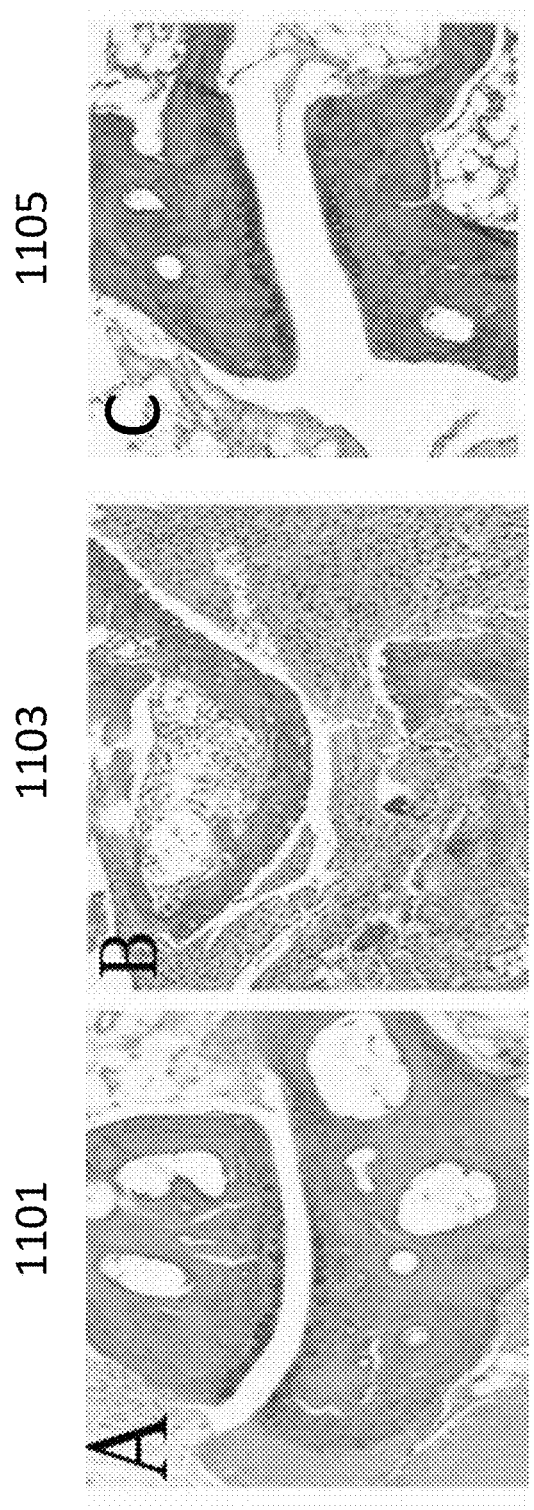
FIG. 11 shows the histologic staining of the hind limb joint sections of the mice having osteoporosis with or without treatment of peptide-gold cluster molecules in accordance with this application.

In reference to FIG. 11, pathologic observation by histology staining shows joint synovial cavity of mouse models with rheumatoid arthritis demonstrating modeling-caused articular cartilage and bone damage. The gold-peptide cluster molecules were capable of protecting articular cartilages and bones from eroding. Image 1101 shows the control group of a normal mouse, Image 1103 shows the collagen II induced mouse model of rheumatoid arthritis, and Image 1105 represents the collagen II induced mouse model of rheumatoid arthritis after injected with 5 mg/kg $gold_{25}$(peptide)$_9$ cluster molecule i.p. for 42 days consecutively. The stains show that gold-peptide cluster molecules can prevent damage and bone erosion to the articular cartilages (Image 1105) in comparison to the model and control groups (Image 1101 and 1103).

Figure 12:
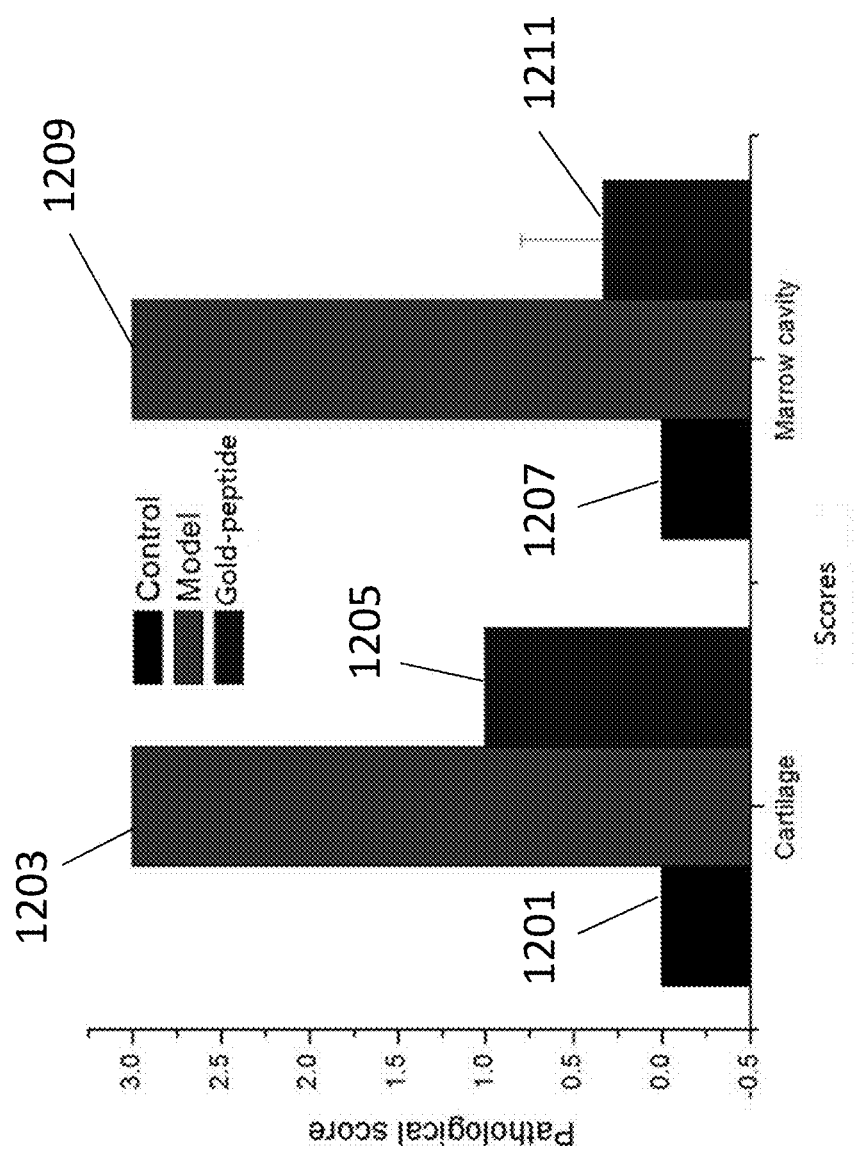
FIG. 12 shows pathological scores of the mice having osteoporosis with or without treatment of peptide-gold cluster molecules in accordance with this application.

FIG. 12 displays the statistical analysis performed after rating on the pathological observation of joint bone damage. The analysis shows that gold-peptide cluster molecules can significantly improve articular cartilage and bone damage in comparison to the pathological model tested.

The inflammation was assessed by means of a visual scoring method where mouse individual paws were graded from 0-4 as follows:
  0 score for having no redness and no swelling;
  1 score for having mild erythema at the toes;
  2 scores for having toe joints and paw swelling;
  3 scores for having swelling below ankle;
  4 scores for having all ankle and paw swelling.

All four limbs of each mouse were examined and scored, and scores of all four limbs were added together for each mouse in each experiment group.

As shown in FIG. 12, the normal mouse group show the lowest pathologic scores at the limbs (bars 1201 and 1207), and collagen II induced arthritic mice show the highest pathologic scores (bars 1203 and 1209), and these high pathologic scores are significantly reduced for arthritic mice treated with $gold_{25}$(peptide)$_9$ cluster molecule i.p. (bars 1205 and 1211), indicating the therapeutic effect of $gold_{25}$(peptide)$_9$ cluster molecule.

Figure 13:
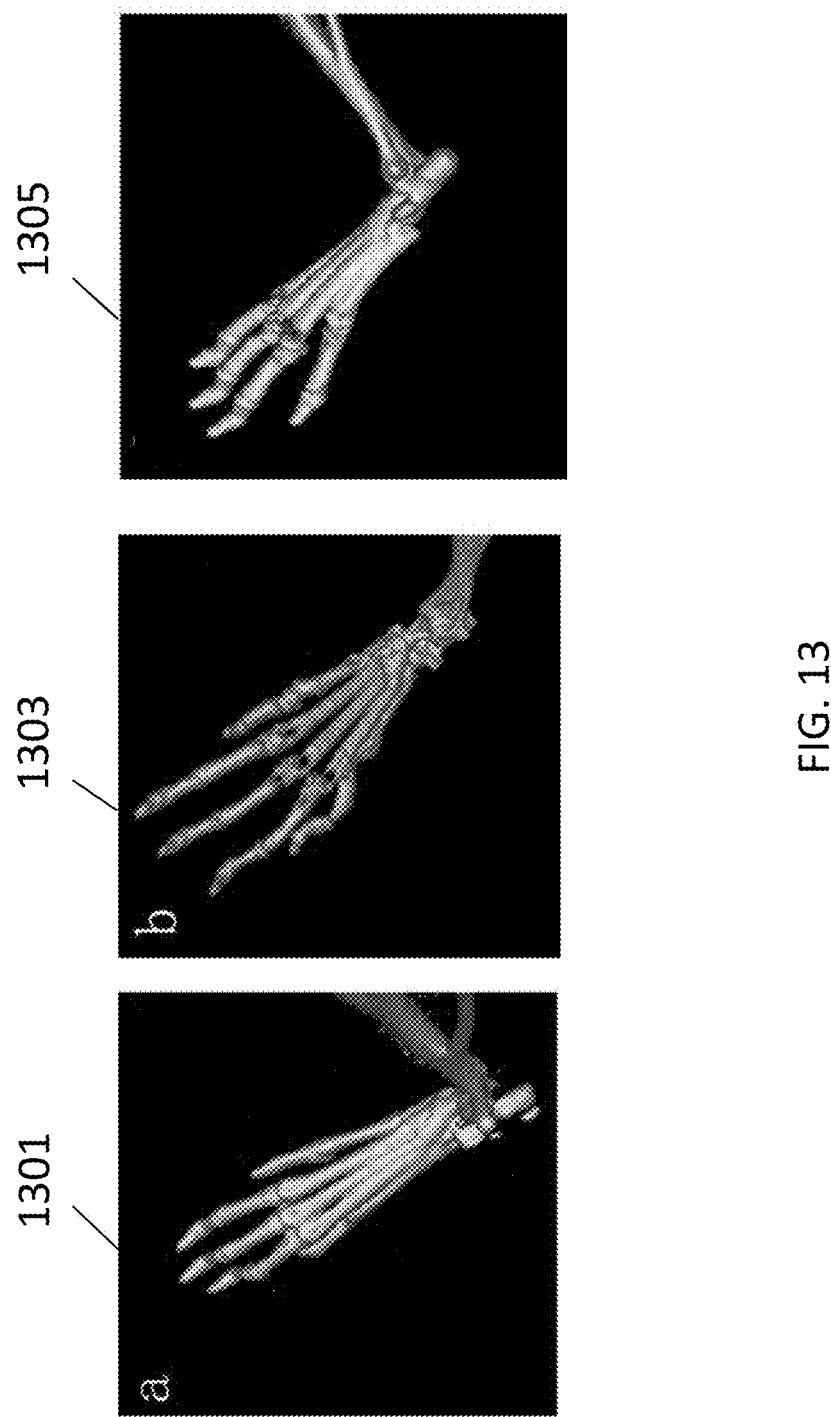
FIG. 13 shows images of the hind limb joint sections of mice having osteoporosis with or without treatment of peptide-gold complex molecules in accordance with this application.

FIG. 13 displays the results of CT scanning of phalanxes of the mouse models for analysis of bone damage. Collagen II arthritis modeling caused bone damage on mice metatarsal joint (image 1303). By injecting gold-peptide cluster molecules, joint damage was significantly relieved demonstrating that the gold-peptide cluster molecules have significant therapeutic effects for bone damage and osteoporosis. Image 1301 shows the paw of a normal mouse with no osteolysis, while image 1303 shows the non-drug treated immunized mouse where type II collagen induced arthritis caused obvious bone deformation and osteolysis at the digital joints. Image 1305 shows the $gold_{25}$(peptide)$_9$ cluster molecule i.p. administered mouse model, where there is significant improvement to the bone density comparing to the non-treated arthritis mice, and has no obvious osteolysis with only slight bone deformation.

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

Additional general background, which helps to show variations and implementations, may be found in the following publications, all of which are hereby incorporated by reference herein for all purposes: N. Ouchi, et al., (2011) "Adipokines in Inflammation and Metabolic Disease," *Nature Reviews,* 11, 85-95; W. Paska, et al., (1986) "Studies on Type II Collagen Induced Arthritis in Mice," *Agents and Actions,* 18, 413-420; K. Phadke, et al., (1985) "Evaluation of the Effects of Various Anti-Arthritic Drugs on Type II Collagen-Induced Mouse Arthritis Model," *Immunopharmacology,* 10, 51-60.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for reducing bone loss in an animal, said method comprising the step of:

preparing a therapeutic agent containing metallic gold cluster molecule agent as an active ingredient wherein said gold cluster molecule agent has a molecular formula: $(gold(0))_n(gold\text{-}cluster\text{-}capping\text{-}molecule)_m$, gold(0) being metallic gold atom as an active ingredient, and gold-cluster-capping-molecule being a polymer molecule that forms non-covalent metal bond with gold(0), n being the number of gold atoms and m being the number of gold-cluster-capping-molecules, $4000 \geq n \geq 3$ and $110 \geq m \geq 4$, wherein said gold cluster molecule is stabilized by said gold-cluster-capping-molecule and emits fluorescence under excitation UV light; and administering a sufficient amount of said therapeutic agent to said animal.

2. The method of claim 1, wherein said step of administering is through oral administration.

3. The method of claim 1, wherein said step of administering is through intraperitoneal administration.

4. The method of claim 1, wherein said step of preparing a therapeutic agent further comprises the step of reacting a gold (I) or a gold (III) salt with a peptide or a protein containing thiol or arginine or selenol or phosphine or amine side group.

5. The method of claim 1, wherein said step of preparing a therapeutic agent further comprises the step of reacting a gold (I) or a gold (III) salt with a peptide or a protein in a solution containing gold-cluster-capping molecules selected from a group consisted of lipids, poly-lysine, poly-arginine, poly-asparagine, poly-aspartic acid sodium salt, poly-aspartic acid sodium salt, poly-glutamate, PEG, PLGA, protein, polysaccharides, nucleic acid, and peptide digestion extracts.

6. The method of claim 1, wherein said peptide or said protein has a sequence of SEQ. ID. NO: 1.

7. The method of claim 1, wherein said peptide or said protein has a sequence of SEQ. ID. NO: 2.

8. The method of claim 4, wherein said protein comprises human serum album.

9. A method for reducing bone loss in an animal, said method comprising the step of:

administering a sufficient amount of a therapeutic agent to said animal wherein said therapeutic agent comprises a metallic gold cluster molecule agent as an active ingredient wherein said gold cluster molecule agent has a molecular formula: $(gold(0))_n(gold\text{-}cluster\text{-}capping\text{-}molecule)_m$, gold(0) being metallic gold atom as an active ingredient and fluorescent, and gold-cluster-capping-molecule being a polymer molecule that forms non-covalent metal bond with gold(0), n being the number of gold atoms and m being the number of gold-cluster-capping-molecules, $4000 \geq n \geq 3$ and $110 \geq m \geq 4$, wherein said gold cluster molecule is stabilized by said gold-cluster-capping-molecule and emits fluorescence under excitation UV light.

10. The method of claim 9, wherein said step of administering is through oral administration.

11. The method of claim 9, wherein said step of administering is through intraperitoneal administration.

12. The method of claim 9, wherein said therapeutic agent is prepared by a step of reacting a gold (I) or a gold (III) salt with a peptide solution or a protein solution wherein said peptide or said protein contains thiol or arginine or selenol or phosphine or amine side group in a solution.

13. The method of claim 9, wherein said therapeutic agent is prepared by a step of reacting a gold (I) or a gold (III) salt with a peptide solution or a protein solution containing gold-cluster-capping molecules selected from a group consisted of lipids, poly-lysine, poly-arginine, poly-asparagine, poly-aspartic acid sodium salt, poly-aspartic acid sodium salt, poly-glutamate, PEG, PLGA, protein, polysaccharides, nucleic acid, and peptide digestion extracts.

14. The method of claim 9, wherein said peptide or protein has a sequence of SEQ. ID. NO: 1.

15. The method of claim 9, wherein said peptide or protein has a sequence of SEQ. ID. NO: 2.

16. The method of claim 12, wherein said protein comprises human serum album.

* * * * *

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial sequence
<220> FEATURE:
<223> OTHER INFORMATION: Synthetic construct
<300> PUBLICATION INFORMATION:
<301> AUTHORS: Liu, R
<302> TITLE: The Au Clusters Induce Tumer Cell Apoptosis Via
      Specifically Targeting Thioredoxin Reductase 1 (TrxR1) and
      Suppressing Its Activity
<303> JOURNAL: Chem Commun
<304> VOLUME: 50
<306> PAGES: 10687-10690
<307> DATE: 2014

<400> SEQUENCE: 1

Cys Cys Tyr Gly Gly Pro Lys Lys Lys Arg Lys Pro Gly
1               5                   10
```

-continued

```
<210> SEQ ID NO 2
<211> LENGTH: 3
<212> TYPE: PRT
<213> ORGANISM: Artificial Sequence
<220> FEATURE:
<223> OTHER INFORMATION: Synthetic construct

<400> SEQUENCE: 2

Glu Cys Gly
1
```